(12) United States Patent
Raykhman et al.

(10) Patent No.: US 8,174,258 B2
(45) Date of Patent: May 8, 2012

(54) METHOD AND SYSTEM FOR MEASUREMENT OF PARAMETERS OF A FLAT MATERIAL

(75) Inventors: Alexander M. Raykhman, East Greenwich, RI (US); Eugene Naidis, Ashkelon, IL (US); Ellis S. Waldman, Providence, RI (US)

(73) Assignee: Dolphin Measurement Systems LLC, Providence, RI (US)

( * ) Notice: Subject to any disclaimer, the term of this patent is extended or adjusted under 35 U.S.C. 154(b) by 460 days.

(21) Appl. No.: 12/426,880

(22) Filed: Apr. 20, 2009

(65) Prior Publication Data
US 2009/0281764 A1 Nov. 12, 2009

Related U.S. Application Data

(63) Continuation-in-part of application No. 11/693,392, filed on Mar. 29, 2007, now abandoned.

(60) Provisional application No. 60/787,272, filed on Mar. 29, 2006.

(51) Int. Cl.
*G01B 7/06* (2006.01)
*G01N 27/72* (2006.01)

(52) U.S. Cl. .......................... 324/228; 324/229; 324/236

(58) Field of Classification Search .......... 324/228–229, 324/236
See application file for complete search history.

(56) References Cited

U.S. PATENT DOCUMENTS

| | | | |
|---|---|---|---|
| 4,053,234 A | 10/1977 | McFarlane | |
| 4,276,480 A | 6/1981 | Watson | |
| 4,298,286 A | 11/1981 | Maxey et al. | |
| 4,658,648 A | 4/1987 | Roddeck et al. | |
| 4,773,760 A | 9/1988 | Makkonen | |
| 5,113,358 A | 5/1992 | Reber | |
| 5,512,823 A | 4/1996 | Nepveu | |
| 5,569,835 A | 10/1996 | Kenney et al. | |
| 5,583,828 A | 12/1996 | Arai et al. | |
| 6,264,793 B1 | 7/2001 | Ojala et al. | |
| 6,380,747 B1 | 4/2002 | Goldfine et al. | |

FOREIGN PATENT DOCUMENTS

JP 2007129196 A 5/2007

OTHER PUBLICATIONS

International Search Report for PCT/US09/48010 dated Feb. 1, 2010.
Applicant: Dolphin Measurement Systems, LLC.

*Primary Examiner* — Bot Ledynh
(74) *Attorney, Agent, or Firm* — Burns & Levinson LLP; Jacob N. Erlich; David W. Gomes

(57) ABSTRACT

A system and method for measurement of parameters of a conductive material, include generating an oscillating electromagnetic field (EMF) interacting with a sample portion from a remotely positioned source; measuring values of components of impedance of the electromagnetic; populating a system of equations including a theory of electromagnetism-based mathematical model of the electromagnetic system; solving the system of equations to calculate values of a distance between the sample portion and the source, thickness of the sample portion in proximity to a point of projection of the source onto the sample portion and electromagnetic properties of the sample portion; outputting the calculated values as the measured values; and repeating the steps of generating, populating, solving, outputting and repeating using the calculated values for the step of populating in place of the measured component values.

43 Claims, 10 Drawing Sheets

| CASE 1, ACTUAL DATA | | | MEASUREMENTS BY THE METHOD OF INVENTION | | | |
|---|---|---|---|---|---|---|
| DISTANCE DEVIATION TOP, mm | DISTANCE DEVIATION BOTTOM, mm | DISTANCE DEVIATION TOP, mm | DISTANCE DEVIATION BOTTOM, mm | THICKNESS mm | THICKNESS MEASUREMENT ERROR, MICRONS | COMMENT |
| 0.068509 | 0.068491 | 0.068540 | 0.06846 | 0.0031809 | 4.666893 | 100 MICRONS MOTION DOWN |
| 0.068909 | 0.068091 | 0.06884 | 0.06816 | 0.0031792 | 3.0169 | 500 MICRONS MOTION DOWN |
| 0.068309 | 0.068691 | 0.068403 | 0.06859 | 0.0031811 | 4.925806 | 100 MICRON UP |
| 0.0679093 | 0.0690907 | 0.068105 | 0.068885 | 3.1779759 | 3.5095 | 500 MICRON UP |

FIG. 6

| CASE 2, ACTUAL DATA | | | MEASUREMENTS BY THE METHOD OF INVENTION | | |
|---|---|---|---|---|---|
| DISTANCE TOP, mm | DISTANCE BOTTOM, mm | DISTANCE TOP, mm | DISTANCE BOTTOM, mm | THICKNESS mm | THICKNESS MEASUREMENT ERROR, MICRONS | COMMENT |
| 0.0669665 | 0.0700335 | 0.06760850 | 0.06951596 | 0.004033 | 0.354858 | |

FIG. 7

| CASE 3, ACTUAL DATA | | | MEASUREMENTS BY THE METHOD OF INVENTION | | |
|---|---|---|---|---|---|
| DISTANCE TOP, mm | DISTANCE BOTTOM, mm | DISTANCE TOP, mm | DISTANCE BOTTOM, mm | THICKNESS mm | THICKNESS MEASUREMENT ERROR, MICRONS | COMMENT |
| 0.0775965 | 0.0594035 | 0.0669665 | 0.0700337 | 0.0040343 | 1.386632 | TRIAL 1 |
| 0.0775980 | 0.059402 | 0.0669638 | 0.0700366 | 0.0043026 | 0.269682 | TRIAL 2 |

FIG. 8

METHOD AND SYSTEM FOR MEASUREMENT OF PARAMETERS OF A FLAT MATERIAL

CROSS REFERENCE TO RELATED APPLICATIONS

This application is a Continuation-in-Part of and claims priority from U.S. patent application Ser. No. 11/693,392, filed Mar. 29, 2007, which claims priority from U.S. Provisional Patent application Ser. No. 60/787,272, filed Mar. 29, 2006, and both of these prior applications are hereby incorporated herein by reference in their entirety.

FIELD OF THE INVENTION

The present invention relates to measurement of linear dimensions and basic electromagnetic parameters of a flat material, and more particularly, to electromagnetic impedance-based methods thereof.

BACKGROUND

Rolling is generally a method of shaping metals from ingots to workable thicknesses for fabrication by passing heated material between compression rollers and under tension. Hot rolling refers to using temperatures above the recrystallization temperature of the particular metal, which leaves the processed metal ductile. Cold rolling refers to using temperatures below the recrystallization temperature for the particular metal, which adds a hardening factor to the processed metal. With the result of thinning the metal, measurement of metal thickness is usually an important part of the process. In view of the harsh environment, non-contact methods of measuring thickness are preferable.

SUMMARY OF THE INVENTION

In one embodiment, the present invention provides a method for measurement of parameters of a conductive material, comprising the steps of: generating an oscillating electromagnetic field (EMF) interacting with a sample portion of flat conductive material, from a source remotely positioned from the sample portion; measuring values of components of impedance of an electromagnetic system including the source of the EMF and the sample portion; populating a system of equations including a theory of electromagnetism-based mathematical model of the electromagnetic system and the measured component values; solving the system of equations to calculate values of a distance between the sample portion and the source, thickness of the sample portion in proximity to a point of projection of the source onto the sample portion and electromagnetic properties of the sample portion; outputting the calculated values as the measured values; and repeating the steps of generating, populating, solving, outputting and repeating using the calculated values for the step of populating in place of the measured component values.

The step of generating the oscillating electromagnetic field interacting with the sample portion of the material may include using a source comprising resistive, inductive and capacitive electrical elements.

The step of measuring values of components of impedance of the electromagnetic system may include the source of the electromagnetic field and the sample portion of the material includes setting at least one driving frequency for the source in the presence of the sample portion. The components of the impedance may include magnitude and phase angle presented in the form of gain-frequency and phase-frequency characteristics of the electromagnetic system. The components of the impedance may include real and imaginary parts. The components of the impedance may be the electromagnetic system's inductance and resistance.

The step of populating a system of equations may include determining an initial estimate of a positional coordinate and a thickness of the sample portion. The positional coordinate may be a distance between the source and the point of projection on a surface of the sample.

The step of populating a system of equations may include determining an initial estimate of parameters and characteristics of said electromagnetic system.

The parameters may include electrical conductivity and magnetic permeability of the material sample and said characteristics are the components of the theoretical impedance of said electromagnetic system obtained with no presence of any conductive material, while the components of said theoretical impedance may be predetermined during the construction of said measuring system. The initial estimate variables may make a vector of initial estimates.

The rolling mill application of the present invention may include the initial estimate of the material sample thickness and positional coordinate being obtainable prior to rolling by measuring with any linear dimension measuring means including but not limited to mechanical, acoustical, laser or electromagnetic devices, such measurements implementing a calibrating function for any non-invasive thickness measuring gauge that does not include a mathematical model of the measurement process of the object of measurement in a measurement algorithm.

The step of populating a system of equations may include measuring a value of a non-zero linear velocity of the sample portion. The step of populating a system of equations may include using material velocity as a known input of the mathematical model.

The step of populating a system of equations may include building at least one correcting function meant for determining adequacy of said mathematical model. The correcting function may be incorporated in said system of equations. The correcting function may be applied to a solution vector of said system of equations. The step of creating may include, application of a vector of initial estimated values for building said correcting function.

The step of populating the system of equations may include monitoring changes in the values of the components of said theoretical impedance of the electromagnetic system. The method may further include monitoring changes in the values of the components of said theoretical impedance of the electromagnetic system by periodically switching a periodical excitation of the electromagnetic measuring circuit to feeding the same circuit with a direct current, thereby effectively nullifying the circuit's ability of sensing surrounding conductive media and delivering at the circuit's output a signal modulated by changes in the circuit's coil resistance and circuits analog electronics transfer functions resulting from changes in the circuit surrounding temperature and ground potential. The monitored changes in the components of the theoretical impedance may be used to modify the mathematical model of the electromagnetic system eliminating dependence of the solution vector on thermal or thermal drift and ground electrical potential disturbances accompanying the process of measurement.

The step of solving the system of equations may include using a recursive numerical solver. The step of solving may include creating an initial guess vector comprised of all or some of the components of said vector of initial estimates to be used for feeding the numerical solver. The initial guess vector may be subsequently replaced by a solution to said system of equations obtained in some preceding executed step of solving.

The step of solving the system of equations may include using a set of formulas analytically representing the solution to said system of equations.

The step of solving the populated system of equations may be comprised of two operations and; with the first operation returning an approximate values for components of the solution vector; and the second operation returning accurate values for components of the solution vector. The method may further include using the approximate values of the vector of solution generated by the first procedure for inputting the second operation to return accurate components of the solution vector, thereby increasing computing speed of the method of the present invention. The method may further include using the approximate values of the vector of solution for generating the guess values vector inputting the numerical solver returning accurate components of the solution vector.

The method may further comprise the step of recording the outputted values of the measured variables in a computer readable medium as a quality control record.

In another embodiment, the present invention provides a method for measurement of positional coordinates, thickness and electromagnetic parameters of a flat conductive material, comprising the steps of: generating an electromagnetic system of oscillating electromagnetic fields interacting with the sample portion of the material from a pair of sources positioned remotely on opposing sides of the sample portion; measuring component values of impedance of the electromagnetic system made by each remote source of electromagnetic field and the material sample; populating a system of equations including the measured impedance component values and a theory of electromagnetism-based mathematical model of the electromagnetic system; solving the system of equations to calculate values of the sample portion distance to each source of EMF, thickness of the sample material in proximity to a point of projection on the sample material by each source of EMF, and the sample material's electromagnetic parameters; outputting the calculated values; repeating the steps of generating, measuring, populating, solving, outputting and repeating.

The pair of sources may be coaxially located on opposing sides of the sample portion.

In still another embodiment of the present invention, a method for adjusting the thickness of flat, electrically conductive material under compressive and tensile forces, comprising the steps of: generating an oscillating electromagnetic field (EMF) interacting with a sample portion of flat, electrically conductive material, from a source remotely positioned from the sample portion; measuring component values of impedance of an electromagnetic system including the source of the EMF and the sample portion; populating a system of equations including the measured component values and a theory of electromagnetism-based mathematical model of the electromagnetic system; solving the system of equations to calculate values of a distance between the sample portion and the source and thickness of the sample portion in proximity to a point of projection of the source in to the sample portion; using the calculated values for adjusting compressive and/or tension forces on the material; repeating the steps of measuring, populating, solving, using and repeating.

In yet another embodiment of the present invention, a method for recording quality control measurements of thickness of a flat conductive material, comprising the steps of: generating an oscillating electromagnetic field (EMF) interacting with a sample portion of flat conductive material, from a source remotely positioned from the sample portion; measuring component values of impedance of an electromagnetic system including the source of the EMF and the sample portion; populating a system of equations including the measured component values and a theory of electromagnetism-based mathematical model of the electromagnetic system; solving the created system of equations to calculate values of a distance between the sample portion and the source and thickness of the sample portion in proximity to a point of penetration of the sample portion by a normal vector to the source; recording the calculated values on a computer readable medium; and repeating the steps of measuring, populating, solving, outputting and repeating. The material may be metal and the compressive and tension forces may be created in a rolling process.

In an even further embodiment, the present invention provides a system for measuring positional coordinates and thickness of a flat conductive material, comprising: an electromagnetic source adapted for generating an oscillating electromagnetic field (EMF) interacting with a sample portion of flat conductive material, wherein the source is remotely positioned from the sample portion; circuitry adapted for measuring component values of impedance of an electromagnetic system including the source of the EMF and the sample portion; and a computing system for solving a system of equations including a theory of electromagnetism-based mathematical model of the electromagnetic system and the measured component values to calculate values of a distance between the sample portion and the source, thickness of the sample portion in proximity to a point of projection of the source onto the material sample portion and electromagnetic properties of the sample portion.

DESCRIPTION OF DRAWINGS

The present invention is illustratively shown and described in reference to the accompanying drawings, in which:

FIG. 6 is a table of measurements taken for one example using the method of the present invention;

FIG. 7 is a table of measurements taken for another example using the method of the present invention;

FIG. 8 is a table of measurements taken for yet another example using the method of the present invention;

DETAILED DESCRIPTION OF THE DRAWINGS

Figure 1:
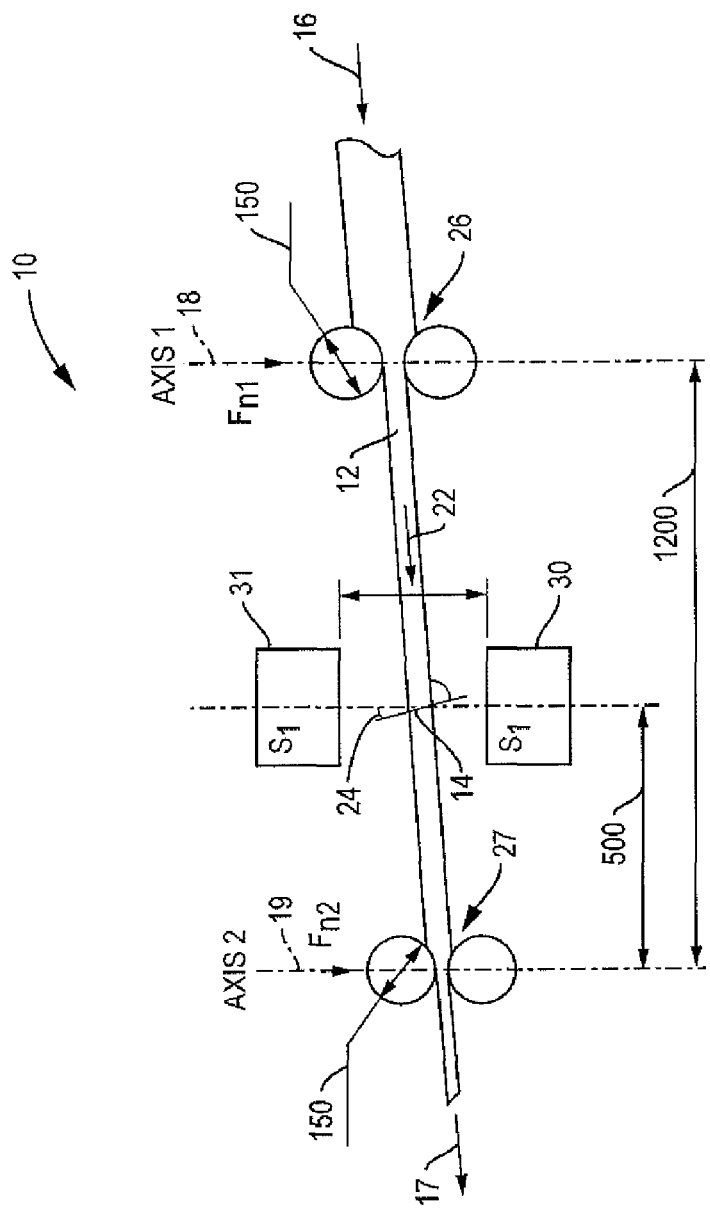
FIG. 1 is a simplified mechanical schematic of a cold rolling process as it would incorporate an embodiment of the present invention.

The present electromagnetic method and system for distance or thickness measurement is accomplished by generating electromagnetic field that interacts with the material creating an electromagnetic oscillating system, which varying electromagnetic energy can be captured by a measuring circuit. The impedance of this circuit is a function of at least the distance between the source of the electromagnetic field and thickness of some layer of the material defined by the skin effect phenomenon.

The method and system are based on an underlying concept that the behavior of a system operating on the electromagnetic energy is governed by the Maxwell's equations mathematically describing the theory of electromagnetism. This theory uses several important variables characterizing the effect of the interaction between the electromagnetic field and the material object. Among them, there are variables relating to the material, such as electric permittivity for non-conductive materials denoted $\epsilon$, electric conductivity denoted $\sigma$ and magnetic permeability denoted $\mu = \mu_0 \mu_r$ for conductive materials, wherein $\mu_0$ denotes magnetic permeability of vacuum and $\mu_r$ denotes relative magnetic permeability of the material. In the more complicated case of moving material, the material speed denoted v has to be added to the group of important variables in order to obtain a better description of the electromagnetic process in the system. The temperature of the material could be added to the group too; however in many practical cases it affects $\epsilon$ or $\sigma$ and $\mu$ without producing noticeable changes to the dimensions of the material. Forces acting upon the material also affect its electromagnetic parameters. In many practical cases, forces change the dimensions of the material, including material thickness, thus causing change to the distance between the source of the electromagnetic field and the material. For the sake of generalization, let the vector of time-dependant variables determining the behavior of the oscillating system be defined as the "vector of substantial coordinates of the dynamic system" and denoted w, and the vector of time-independent variables determining the behavior of the oscillating system be defined as the "vector of substantial parameters of the dynamic system" and denoted $\xi$.

Within the framework of this concept, the distinction between the useful components of the w and variables of disturbance in the w can be made only by assignment based on the specifics of the particular project. The correctness of this conclusion is supported by the fact that for the most general case, all components of the vectors w and $\xi$ are the equally important elements of the system of Maxwell's equations defining the behavior of any electromagnetic system. Therefore, an accurate measurement of any of the above described variables requires either compensation or monitoring of the rest of the elements of the vector w. The present method provides for the simultaneous determination of all components of w.

The combination of the environmental and technological factors in various applications, including that of a cold-rolling steel mill, often makes impossible obtaining an accurate measurement of the material thickness or distance to the source of the electromagnetic field (EMF) interacting with the material. Although the method of the present invention is not limited by the material type, the present embodiment deals with ferrous materials. Therefore, the description of the method will be made by the example of the metal strip thickness measurement during the cold rolling of the flat ferromagnetic strip. Despite the fact that the speed of the material directly affects the measuring circuit impedance, in many practical applications, the material speed is measurable by known means and therefore can be excluded from the list of unknown variables in the description of the method.

A simplified mechanical schematic of the cold rolling mechanism 10 and process is shown in the FIG. 1. One exemplary embodiment, the various process parameters can include strip material 12, such as carbon steel, strip thickness 14 (1.0-7.5 mm), tensile force $F_t$ 16, 17 (0-20 tons); Normal force $F_n$ 18, 19 (0-400 tons); roll linear speed v 22 (0-3 m/s), and pass line angle 24 (0-10°). Electromagnetic field (EMF) sources 30, 31 are used to project an EMF through strip 12.

It follows from FIG. 1 that the moving strip material 12 changes its thickness 14 in response to the simultaneous application of tensile 16, 17 and compressive 18, 19 forces. Friction and mashing at the roll bite 26, 27 causes a temperature increase of the strip that together with the forces and bending torques acting at the strip causes changes in the conductivity and magnetic permeability of the strip material 12 and any layers thereof, with its rate of change increasing from the center layer to the external layers of the strip due to the skin effect. Therefore, the impedance of the oscillating circuit that is established between the sources 30, 31 of the electromagnetic field and the material are affected at the same time by the changing thickness of the material and by the rest of the factors described in this paragraph.

Figure 2:
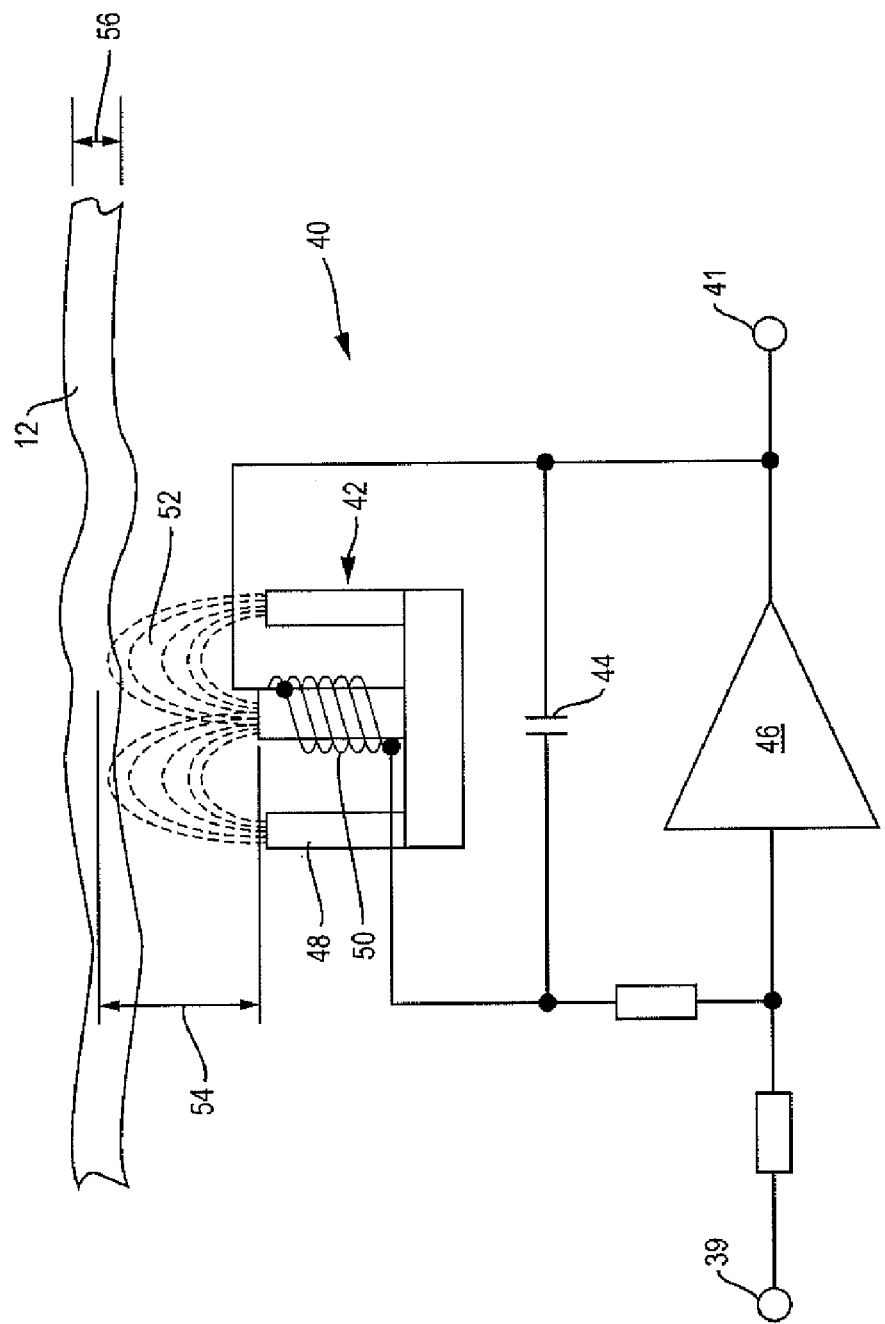
FIG. 2 is an illustration of an electromagnetic oscillating circuit constructed in accordance with one embodiment of the present invention.

A simplified illustration of the idea of the measuring electromagnetic circuit 40 is shown in the FIG. 2 in relation to a test material such as a metal strip 12. The basic circuit includes an electromagnetic coil 42 connected in parallel to a capacitor 44 and driven by an amplifier 46. Coil 42 includes an E-profile core having a central winding 50 and adapted to project magnetic flux lines 52 in the direction of metal strip 12. The amount of magnetic flux lines 52 reaching strip 12 depends upon the distance 54 between coil 42 and metal strip 12 as well as the thickness 56 of strip 12. In practice, circuit 40 may be driven by a variable frequency signal at input 39 and the frequency dependent gain may be measured at output 41. The inductive interaction of strip 12 on coil 42 affects the impedance of circuit 40, represented for example by its gain and phase vs. excitation frequency curves.

Figure 3:
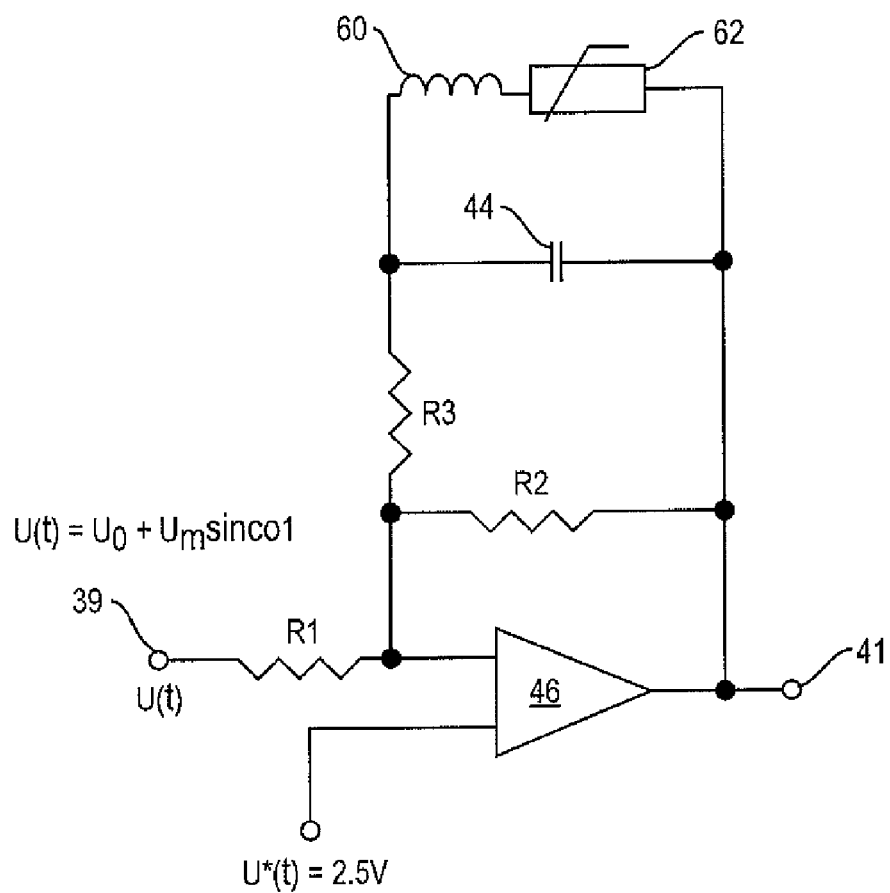
FIG. 3 is a schematic of the electromagnetic oscillating system representing the embodiment of FIG. 2.

FIG. 3 is a schematic of the system illustrated in FIG. 2, which identical components are labeled the same as FIG. 2. A coil 60 represents the combined inductance of coil 42 and its interaction with metal strip 12, both of FIG. 2.

Figure 4:
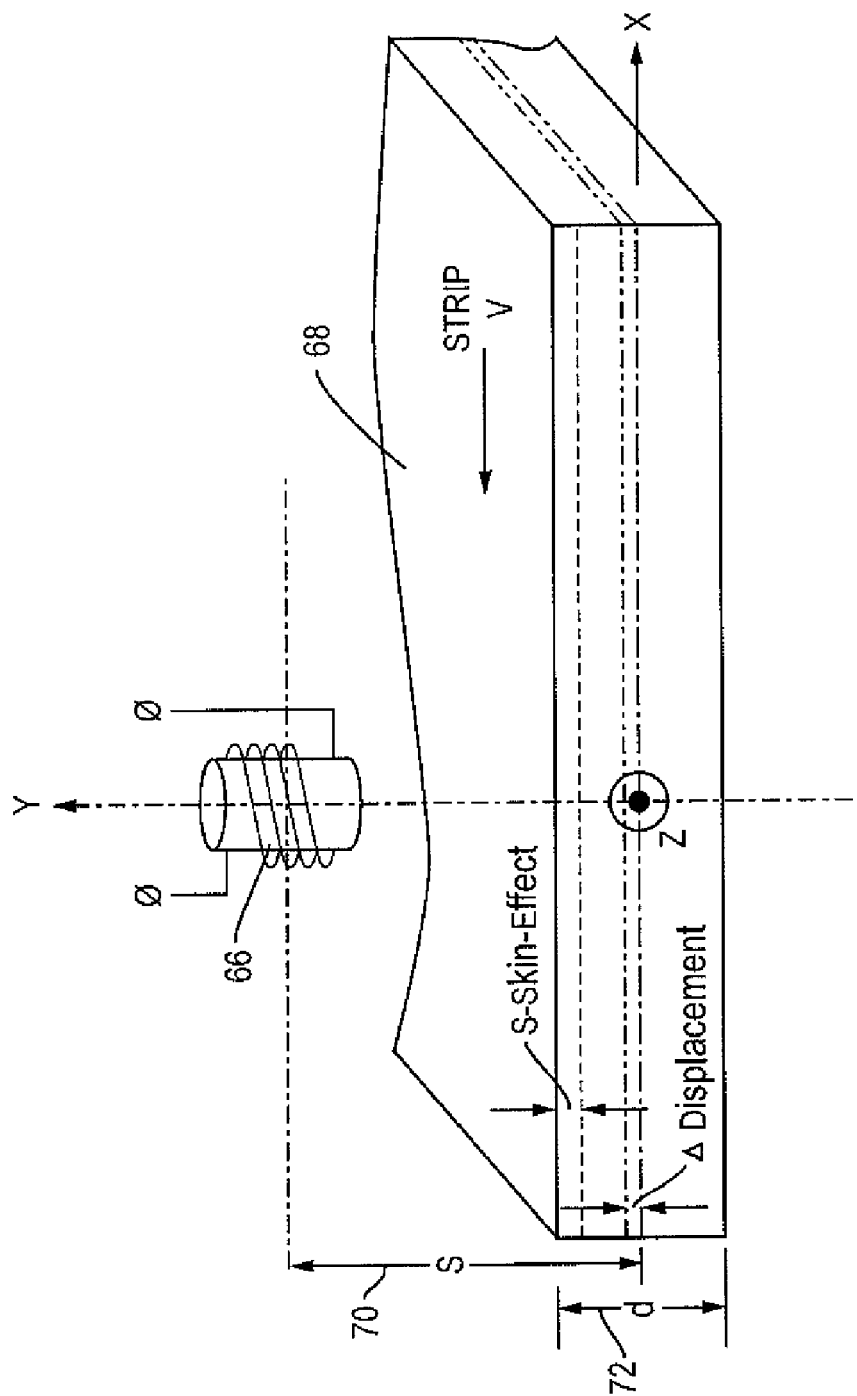
FIG. 4 is a perspective diagram of the relationship between an electromagnetic source and a material under test as used by the embodiment of FIGS. 1-3.
Figure 5A:
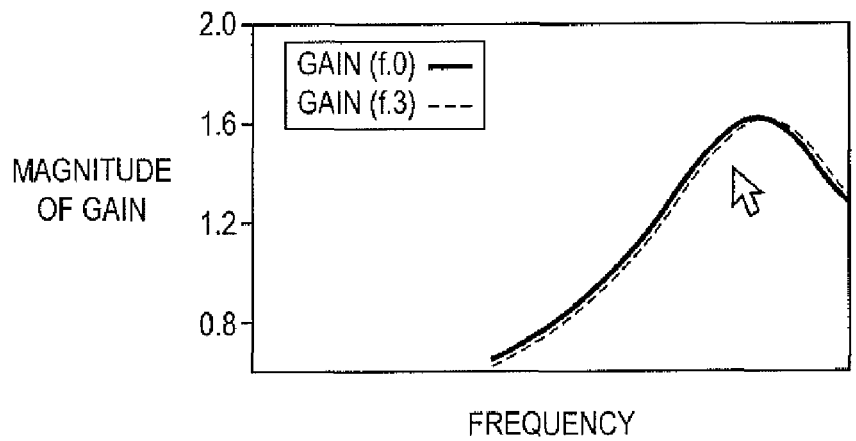
FIGS. 5A and 5B are graphs of the gain and the phase angle vs. frequency for the measuring circuit EM system of FIGS. 1-4.
Figure 5B:
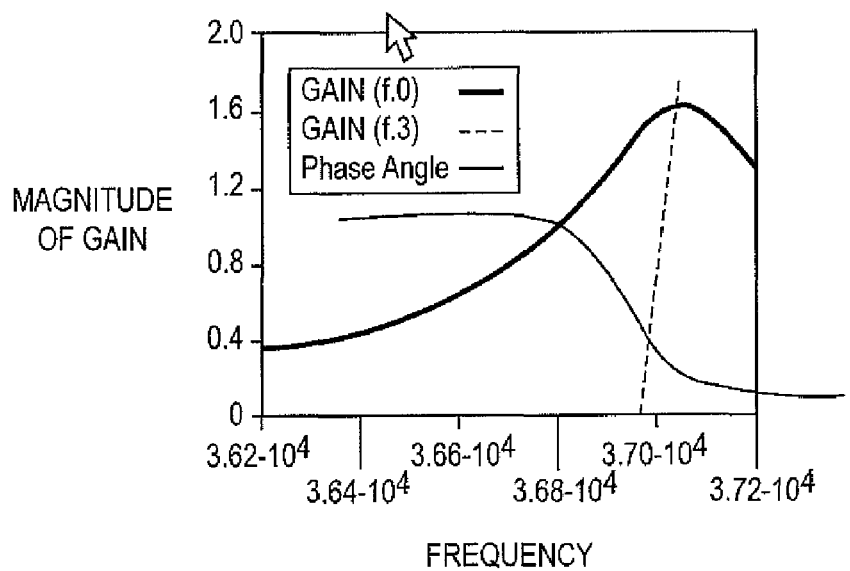

For the further description of the method, a system of coordinates {x, y, z} is established and depicted in the FIG. 4 in relation to a coil 66 and a metal strip 68. The distance s 70 of strip 68 from coil 66 is shown along with the thickness d 72 of strip 68.

The method of the present invention utilizes a continuously oscillating or alternating electromagnetic field that is excited by an external periodical signal having the frequency denoted by $f_0 \gg f$, wherein f denotes the highest frequency of any noticeable mechanical process accompanying the movement of the material. The method can be described in the "language" of complex impedance; any legitimate representation of it such as frequency-response characteristics that can be a gain-frequency characteristic and a phase-response characteristic, frequency-dependent real and imaginary part of the complex impedance, or complex inductance represented by the measuring electromagnetic system's inductance and resistance. The use of any of the listed frequency-response characteristics do not alter the main sequence of operations of the method of the present invention as soon as these characteristics fully represent the measuring system's complex impedance. The inductance and resistance of the oscillating circuit will be used in an embodiment of the method.

One embodiment of the invention assumes the use of two sources of electromagnetic field positioned above (top circuit) and below (bottom circuit) the metal strip; their position is indicated in mathematical description of the method by the index j=(top, bottom or t,b). This index will appear in the formulas when it is important to know about the position of the source of electromagnetic field, otherwise the j-index will be omitted for the sake of simplicity of the method disclosure. Let the circuit's inductance be denoted $L(w,\xi,f_0)$ or $L_j(w_j,\xi_j,f_{0j})$ and the circuit's resistance be denoted $R(w,\xi,f_0)$ or $R_j(w_j,\xi_j,f_{0j})$. Following the logic of the method's mathematical description, the driving frequency $f_0$ measured in Hz can be substituted with its angular equivalent $\omega_0$ measured in rad/s. In the preferred application of the method $w=\{s,d,\mu,\sigma\}$, wherein s—distance between the designated point in the source of the electromagnetic field and the central layer of the strip; d—strip thickness; $\sigma$—strip electrical conductivity, $\mu$—strip magnetic permeability.

According to the method of the present invention, a simultaneous measurement of some or all the components of the vector w is performed by solving the following system of equations:

$$\begin{cases} L_m(\omega_0)_j - L_c(w, \xi, \omega_0)_j = 0 \\ R_m(\omega_0)_j - R_c(w, \xi, \omega_0)_j = 0 \\ s_t + s_b = const, \ j = (t, b) \end{cases} \quad (0.1)$$

Wherein, index m shows that the circuit's inductance/resistance is measured by the inductance/resistance measuring means; index c shows that the circuit's inductance/resistance is calculated using the Maxwell's Equations application to the particular configuration of the magnetic system of the preferred embodiment.

In the preferred application example, the mathematical model of the electromagnetic circuit has the following view:

$$\begin{cases} L_m(\omega_0)_j - [L_{0j}F_1(u, \xi, \omega_0)_j - 2R_{0j}F_2(u, \xi, \omega_0)_j] = 0 \\ R_m(\omega_0)_j - [2L_{0j}F_2(u, \xi, \omega_0)_j + R_{0j}F_1(u, \xi, \omega_0)_j] = 0 \\ s_t + s_b = const, \ j = (t, b) \end{cases} \quad (0.2)$$

Wherein, $L_0$ denotes the inductance of the source of electromagnetic field with no presence of conductive medium; $R_0$ denotes the resistance of the source of electromagnetic field with no presence of conductive medium. The vector u in the (0.2) is defined as follows:

$$u = \{s, d, z\} \quad (0.3)$$

$$z = \sqrt{\frac{2\mu_r}{\omega_0\mu_0\sigma}}$$

The transition from the vector w of the (0.1) to the vector u of the (0.2) equalizes the number of unknowns with the number of equations in the system (0.2).

In many practical cases, it is challenging to build a mathematical model absolutely adequate to the physical object this model represents. The source of the electromagnetic field, that in the present embodiment includes an oscillating circuit having an inductance coil as an important part thereof, may belong to this class of physical objects. Therefore, the system of equations (1.2) can be transformed to the following two $$\begin{cases} L_m(\omega_0)_j - [L_{0j}F_1(u, \xi, \omega_0)_j - 2R_{0j}F_2(u, \xi, \omega_0)_j + L_{cr}(u^*, \xi, \omega_0)_j] = 0 \\ R_m(\omega_0)_j - [2L_{0j}F_2(u, \xi, \omega_0)_j + R_{0j}F_1(u, \xi, \omega_0)_j + R_{cr}(u^*, \xi, \omega_0)_j] = 0 \\ s_t + s_b = const, \ j = (t, b) \end{cases} \quad (0.4)$$

$$\begin{cases} u_{ij} = F_{cr}(\hat{u}, u^*, \omega_0) \\ L_m(\omega_0)_j - [L_{0j}F_1(\hat{u}, \xi, \omega_0)_j - 2R_{0j}F_2(\hat{u}, \xi, \omega_0)_j] = 0 \\ R_m(\omega_0)_j - [2L_{0j}F_2(\hat{u}, \xi, \omega_0)_j + R_{0j}F_1(\hat{u}, \xi, \omega_0)_j] = 0 \\ s_t + s_b = const, \ j = (t, b) \end{cases} \quad (0.5)$$

Wherein in the equations (0.4), $L_{cr}$ denotes a correcting member for the math model of inductance and $R_{cr}$ denotes a correcting member for the math model of resistance, u* is a vector of initial estimate of the vector u serving also as a solution guess value vector in the case of numerically solved system of equations (0.4). In the system (0.5), vector u denotes a more accurate corrected solution of the system of equations (0.2) whose solution is denoted by the vector $\hat{u}$. The procedure returning the initial estimate vector is titled the Initialization Procedure.

In the preferred embodiment of the method of the present invention, the functions $F_1(u,\xi,w_0)_j$ and $F_2(u,\xi,w_0)_j$ can be presented in the following format:

$$F_1(u, \xi, \omega_0) = \frac{E^2(Z+1)^2 - (Z-1)^2 + E^2 - 1}{[E(Z+1) - Z + 1]^2 + (E+1)^2} \quad (0.6)$$

$$F_2(u, \xi, \omega_0) = \frac{2EZ}{[E(Z+1) - Z + 1]^2 + (E+1)^2}$$

$$E = e^{k(2s-d)}$$

An inclusion of the expressions (0.6) into the equations (0.4) or (0.5) returns an approximate analytical solution for the variables $(E_j, Z_j)$, j=(t,b) and consequently for the sought variable d representing the thickness of the strip:

$$U(Q, R) = (Q^4 + 8Q^2R^2 - 2Q^2 + 16R^4 + 24R^2 + 1)^{\frac{1}{2}} \quad (0.7)$$

$$E_{v1} = \frac{Q^4 + [8R^2 - 4R + 2 + U(Q, R)]Q^2 + 16R^4 - 16R^3 + 24R^2 + 4R + [4R(R-1)-1]U(Q, R) + 1}{[Q^2 + 4R^2 + U(Q, R) - 1](4R^2 + Q^2 - 2Q - 1)}$$

$$Z_{v1} = \frac{1}{4R}[Q^2 + 4R^2 + U(Q, R) - 1]$$

$$E_{v2} = \frac{Q^4 + [8R^2 - 4R - 2 - U(Q, R)]Q^2 + 16R^2 - 16R^3 + 24R^2 + 4R - [4R(R-1)-1]U(Q, R) + 1}{[Q^2 + 4R^2 - U(Q, R) - 1](4R^2 + Q^2 - 2Q + 1)}$$

$$Z_{v2} = \frac{1}{4R}[Q^2 + 4R^2 - U(Q, R) - 1]$$

$$Q_v = \frac{R_{mv}R_{0v} + L_{0v}\omega_v^2 L_{mv}}{L_{0v}^2\omega_v^2 + R_{0v}^2}$$

$$R_v = \frac{1}{2}\omega \frac{L_{0v}R_{mv} - L_{mv}R_{0v}}{L_{0v}^2\omega_v^2 + R_{0v}^2}$$

$$v = (t, b)$$

$$d = \text{Gap} - \frac{1}{2k}\ln(E_b E_t)$$

The formulas (0.7) provide a mathematical description of the coarse subsystem measuring the metal strip parameters—components of u* and feeding the values of the vector u* at the beginning of each measuring cycle into the fine numeric measuring subsystem described by the equations (0.4) or (0.5), thereby generating the solutions guess vector required for the execution of the algebraic equations solving numerical algorithm of the method of the present invention.

Figure 10:
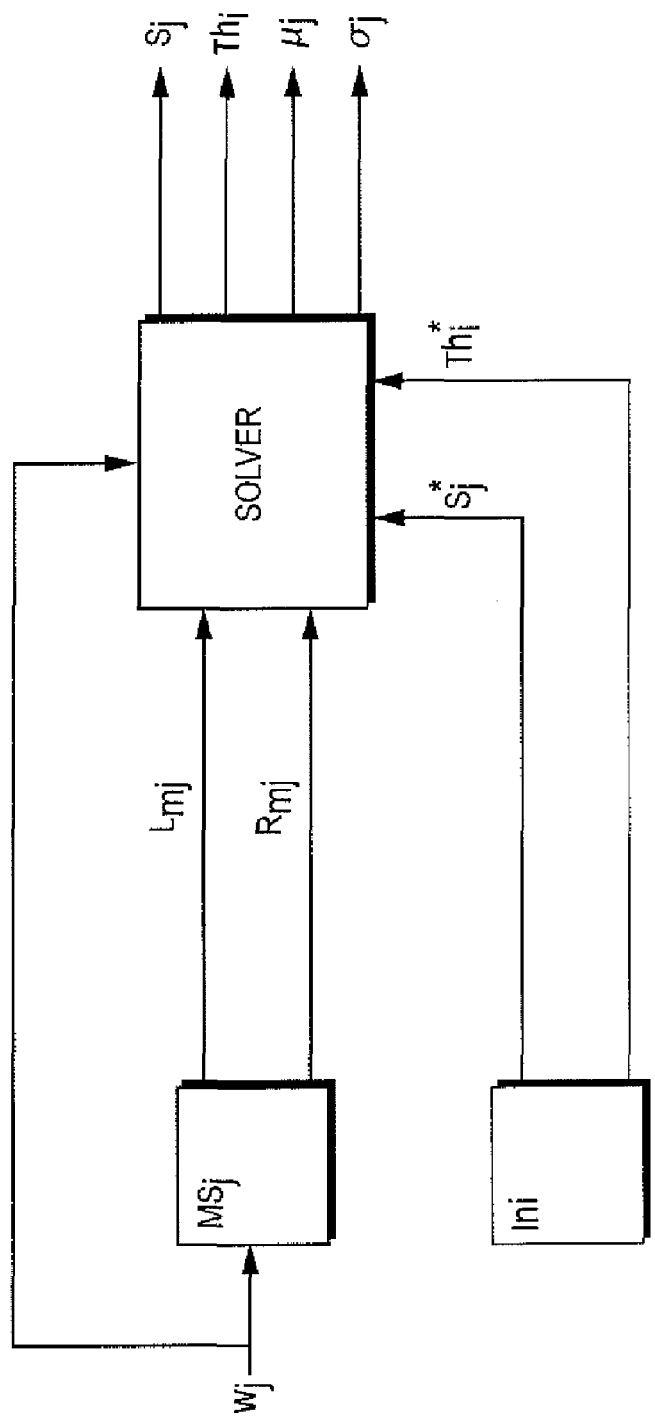
FIG. 10 is a block diagram of a computational system suitable for use with the present invention.
Figure 11:
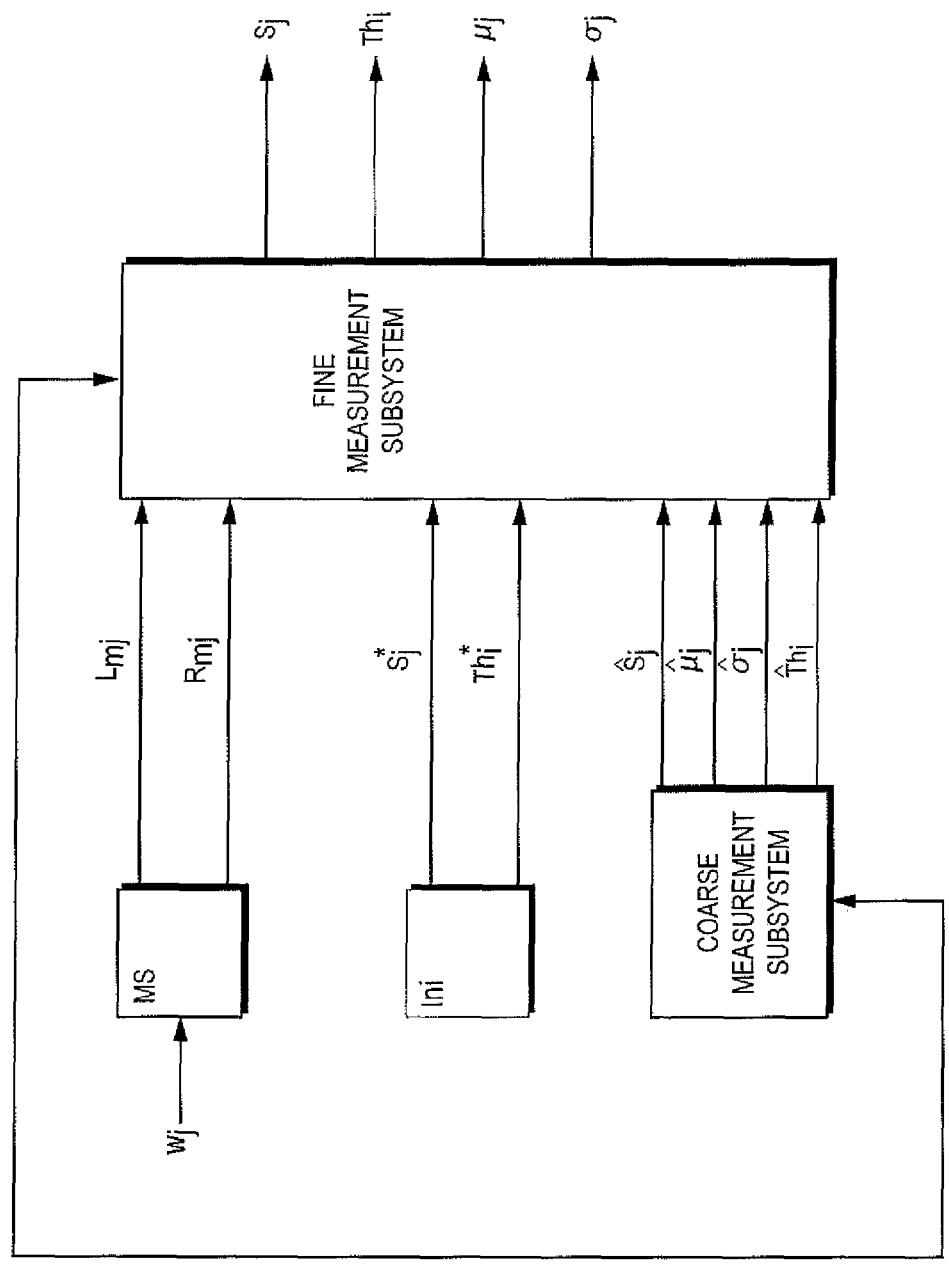
FIG. 11 is a block diagram of another computational system suitable for use with the present invention.

Depending on the technical application specification, the entire measuring system of the present invention can be constructed with or without including the coarse measurement subsystem in its architecture. The selection criteria is based on the estimated range of variables that are supposed to be measured. For example, measuring the steel strip thickness between 0.5 mm and 1.0 mm can be achieved by using a mono-type system having a block diagram shown in the FIG. 10. Measuring the steel strip thickness between 0.25 mm and 9.0 mm may require using a combined system having a block diagram shown in the FIG. 11.

The Initialization Procedure is an important block in the measurement algorithm and therefore should be described with more details. According to (0.4), the values for the correcting members $L_{cr}(w^*,\xi,\omega_0)_j$, $R_{cr}(w^*,\xi,\omega_0)_j$ can be determined using formulas:

$$\begin{cases} L_{cr}(w^*, \xi, \omega_0)_j = L_{0j}F_1(w^*, \xi, \omega_0)_j - 2R_{0j}F_2(w^*, \xi, \omega_0)_j - L_m(\omega_0, s^*, d^*)_j \\ R_{cr}(w^*, \xi, \omega_0)_j = 2L_{0j}F_2(w^*, \xi, \omega_0)_j + R_{0j}F_1(w^*, \xi, \omega_0)_j - R_m(\omega_0, s^*, d^*)_j \end{cases} \quad (0.8)$$

Wherein the measured members $L_m(\omega_0,s^*,d^*)_j$ and $R_m(\omega_0, s^*,d^*)_j$ are associated with the measured values $(s^*,d^*)_j$ prior to rolling. Measuring of the $(s^*,d^*)_j$ is achievable by means of any measuring instrument which accuracy and precision satisfy the requirements of the measurement application. For example, acoustic, laser, or mechanical measuring devices could be employed. It is important to note that an application of the above-described initialization procedure to any non-invasive thickness gauge utilizing a direct measurement paradigm that does not require the simulating model to participate in the measurement process, includes a built-in calibration into a measurement algorithm that in the case of radiometric thickness gauges obviates the need in expensive, maintenance-heavy magazines of material samples, which matching with the physical-chemical composition of the measured strip is a prerequisite of the accurate thickness measurement by radiometric gauges.

Another substantial problem affecting every high-accuracy electromagnetic measuring system is thermal drift of the device's output signal. Despite the fact that drift at the output of the measuring circuit was no greater than 0.05% per C.°, it produced unwanted deviations of the measured thickness in laboratory trials; the targeted repeatability of measurement was 0.1% of the nominal thickness set point that in the case of 1 mm thickness sample equaled to 1 micron. Therefore, the measurement system of the present invention was equipped with a drift monitoring channel (DMC), which algorithm is disclosed below. The DMC switches the entire measuring circuit from being excited at the driving frequency $\omega_0$—"measurement" to being fed by some DC current, thereby providing for monitoring of the internal changes in parameters of the measuring circuit, the coil primarily—"drift monitoring". The DC output is associated with the shape of the $$L_{0j}=L_{0j}(\omega_0,t)=L_{0j}(\omega_0,u_{DC}) \text{ and } R_{0j}=R_{0j}(\omega_0,t)=R_{0j}(\omega_0,u_{DC}) \quad (0.9)$$

It follows from the expressions (0.9) that the dependence of the measuring circuit impedance with no metal present is converted in the equivalent dependence of the circuit impedance on the circuit output value originated by the DC voltage o current feeding the circuit. In one embodiment of the method of the present invention such dependences are represented by the formula:

$$S_{0j}(f)=S'(f,u)_j+(\alpha'_j+\alpha''_j\Delta u_{DCj})f_j+\beta'_j+\beta''_j\Delta u_{DCj}$$

$$S=(L_0,R_0), j=(t,b) \quad (0.10)$$

To illustrate the method of the present invention, an application of the method to the case of an immobile flat metal sample having uniform electromagnetic properties throughout the sample thickness is presented below.

Wherein, $(\bar{\mu},\bar{\sigma})$ denote standard values for the material sample's magnetic permeability and conductivity respectively. It follows from the (0.6) that the values for the correcting members $L_{cr}(w^*,\xi,\omega_0)_j$, $R_{cr}(w^*,\xi,\omega_0)_j$ were determined using formulas:

$$\begin{cases} L_m(\omega_0)_j - [L_{0j}F_1(w, \xi, \omega_0)_j - R_{cr}(u^*, \xi, \omega_0)_j L_{cr}(w^*, \xi, \omega_0)_j] = 0 \\ R_m(\omega_0)_j - [2L_{0j}F_2(w, \xi, \omega_0)_j + R_{0j}F_1(w, \xi, \omega_0)_j + R_{cr}(w^*, \xi, \omega_0)_j] = 0 \\ s_t + s_b = const \end{cases} \quad (0.11)$$

$$w = \{s, d, \mu, \sigma\}, w^* = \{s^*, d^*, \overline{\mu}, \overline{\sigma}\}, j = (t, b)$$

Wherein, $(\overline{\mu}, \overline{\sigma})$ denote standard values for the material sample's magnetic permeability and conductivity respectively.

The system of governing equations (0.11) was solved numerically against the vector $w=\{s,d,\mu,\sigma\}$ in three case studies described in the tables of FIGS. 6-8.

Although not limited thereto, in these case studies, the pre-measured components of the vector W had the following values: Metal Sample: flat metal strip, $12 \times 12$ in$^2$, carbon steel alloy 1020.

Case 1. Material Sample Moved Vertically from Initial Position Between the Two Non-Interfering Sources of EMF. See FIG. 6.

$s^*_{top}$=0.06840937 m $s^*_{bottom}$=0.06859063 m $d^*$=0.00317625 m $\overline{\mu}_{r\,top}$=100

$\overline{\mu}_{r\,bottom}$=100

$\overline{\sigma}_{top}$=6.54·10$^6$ Siemense/m $\overline{\sigma}_{bottom}$=6.54·10$^6$ Siemense/m Case 2. See FIG. 7.

$s^*_{top}$=0.074729 m $s^*_{bottom}$=0.062271 m $d^*$=0.002998 m $\overline{\mu}_{r\,top}$=330

$\overline{\mu}_{r\,bottom}$=330

$\overline{\sigma}_{top}$=25·10$^6$ Siemense/m $\overline{\sigma}_{bottom}$=25·10$^6$ Siemense/m Step-Thickness Material Sample
(Initialization on the first thickness sample area, $d^*$=0.002998 m; measurement on the second thickness sample area, $d^*$=0.004033 m)

Case 3. See FIG. 8

$s^*_{top}$=0.0775965 m $s^*_{bottom}$=0.0594035 m $d^*$=0.004033 m $\overline{\mu}_{r\,top}$=100

$\overline{\mu}_{r\,bottom}$=100

$\overline{\sigma}_{top}$=6.54·10$^6$ Siemense/m $\overline{\sigma}_{bottom}$=6.54·10$^6$ Siemense/m Measurement System is Initialized, Material Sample is Fast-Heated from 25 C.° to 65 C.° before Measuring The above-presented application of the method of the invention supported measurement of thickness of the flat metal strip with an average measurement error no greater than 0.1% of the sample actual thickness regardless of the material vertical motion and changes of the material sample temperature that makes the proposed method applicable to the majority of industrial technologies utilizing measuring thickness of flat conductive materials.

It follows from the proposed method of measurement that any component of the vector of substantial coordinates w of the oscillating circuit could be determined by sequentially performing the operations of the method after the variables are broken down in coordinates and parameters of the oscillating circuit. The composition of the vector w is defined by the technical specification regulating the particular application and implementation of the method.

The practical applications of the method of the present invention include a system in which the thickness of a metal strip may be measured during various metal rolling processes, such as cold rolling or slitting. Such measurements may be done for recording of quality assurance data or any other suitable part of a thickness control process. Another potential application of the present invention is the measurement of a coating or layer thickness in a plating process.

Figure 9:
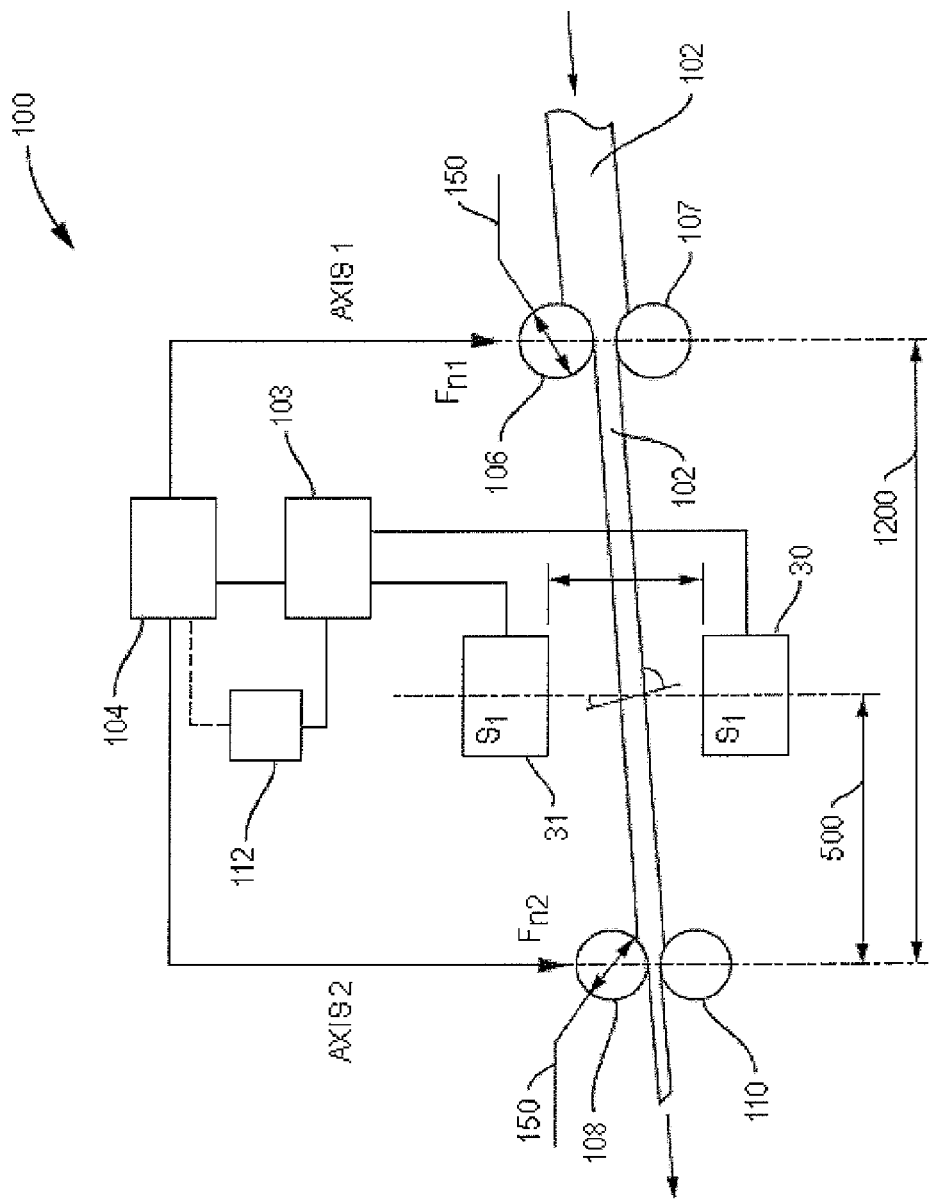
FIG. 9 is a schematic diagram of a system for controlling the thickness of a metal during cold rolling processing.

FIG. 9 is a schematic diagram of a portion 100 of a metal rolling system in which the thickness of a metal strip 102 is measured. Electrical information from EMF sources 30, 31 is coupled to a computation system 103 which uses the above described process to calculate thickness of the metal strip 102. Computation system 103 passes the resulting thickness measurement to any suitable control system 104 for the process of system portion 100. Thickness measurement data may be recorded on a computer readable medium 112 for quality assurance purposes either directly from computation system 103 or indirectly through control system 104.

In the manner described above, the present invention provides a method and system for linear dimension measurement, wherein distance and thickness are the particular cases thereof; the method invariant to electromagnetic properties of the flat, electrically conductive material including its conductivity and permeability The present invention also provides a method and system for determination of the flat material basic electromagnetic parameters including but not limited to the material conductivity and magnetic permeability; the method invariant to the thickness of the material and the distance between the material and the source of the electromagnetic field, and the material speed.

Although the preferred embodiment has been described in detail, it should be understood that various changes, substitutions and alterations can be made therein without departing from the spirit and scope of the invention.

What is claimed is:

1. A method for measurement of parameters of a conductive material, comprising the steps of:
   generating an oscillating electromagnetic field (EMF) interacting with a sample portion of flat conductive material, from a source remotely positioned from the sample portion;
   measuring values of components of impedance of an electromagnetic system including the source of the EMF and the sample portion;
   populating a system of equations including a theory of electromagnetism-based mathematical model of the electromagnetic system and the measured component values;
   solving the system of equations to calculate values of a distance between the sample portion and the source, thickness of the sample portion in proximity to a point of projection of the source onto the sample portion and electromagnetic properties of the sample portion;
   outputting the calculated values as the measured values; and
   repeating the steps of generating, populating, solving, outputting and repeating using the calculated values for the step of populating in place of the measured component values.

2. The method of claim 1 wherein the step of generating the oscillating electromagnetic field interacting with the sample portion of the material includes using a source comprising resistive, inductive and capacitive electrical elements.

3. The method of claim 1 wherein the step of measuring values of components of impedance of the electromagnetic system including the source of the electromagnetic field and the sample portion of the material includes setting at least one driving frequency for the source in the presence of the sample portion.

4. The method of claim 3 wherein the components of the impedance include magnitude and phase angle presented in the form of gain-frequency and phase-frequency characteristics of the electromagnetic system.

5. The method of claim 3 wherein the components of the impedance include real and imaginary parts.

6. The method of claim 3 wherein the components of the impedance are the electromagnetic system's inductance and resistance.

7. The method of claim 1 wherein the step of populating a system of equations includes determining an initial estimate of a positional coordinate and a thickness of the sample portion.

8. The method of claim 7 wherein the positional coordinate is a distance between the source and the point of projection on a surface of the sample.

9. The method of claim 1 wherein the step of populating a system of equations includes determining an initial estimate of parameters and characteristics of said electromagnetic system.

10. The method of claim 9 wherein said parameters include electrical conductivity and magnetic permeability of the material sample and said characteristics are the components of the theoretical impedance of said electromagnetic system, and
   further wherein the components of said theoretical impedance are predetermined.

11. The method of claim 9 wherein all initial estimate variables make a vector of initial estimates.

12. The method of claim 11 wherein in a rolling mill application of the present invention, the initial estimate of the material sample thickness and positional coordinate is obtainable prior to rolling by measuring with any linear dimension measuring means including but not limited to mechanical, acoustical, laser or electromagnetic devices,
   such measurements implementing a calibrating function for any non-invasive thickness measuring gauge that does not include a mathematical model of the measurement process of the object of measurement in a measurement algorithm.

13. The method of claim 1 wherein the step of populating a system of equations includes measuring a value of a non-zero linear velocity of the sample portion.

14. The method of claim 13 wherein the step of populating a system of equations includes using material velocity as a known input of the mathematical model.

15. The method of claim 1 wherein the step of populating a system of equations includes building at least one correcting function meant for determining adequacy of said mathematical model.

16. The method of claim 15 wherein said correcting function is incorporated in said system of equations.

17. The method of claim 15 wherein said correcting function is applied to a solution vector of said system of equations.

18. The method of claim 15 wherein the step of creating includes application of a vector of initial estimated values for building said correcting function.

19. The method of claim 1 wherein the step of populating the system of equations includes monitoring changes in the values of the components of said theoretical impedance of the electromagnetic system.

20. The method of claim 19 further including monitoring changes in the values of the components of said theoretical impedance of the electromagnetic system by periodically switching a periodical excitation of the electromagnetic measuring circuit to feeding the same circuit with a direct current, thereby effectively nullifying the circuit's ability of sensing surrounding conductive media and delivering at the circuit's output a signal modulated by changes in the circuit's coil resistance and circuits analog electronics transfer functions resulting from changes in the circuit surrounding temperature and ground potential.

21. The method of claim 19 wherein said monitored changes in the components of the theoretical impedance are used to modify the mathematical model of the electromagnetic system eliminating dependence of the solution vector on thermal or thermal drift and ground electrical potential disturbances accompanying the process of measurement.

22. The method of claim 1 wherein the step of solving the system of equations may include using a recursive numerical solver.

23. The method of claim 22 wherein the step of solving includes creating an initial guess vector comprised of all or some of the components of said vector of initial estimates to be used for feeding the numerical solver.

24. The method of claim 23 wherein the initial guess vector is subsequently replaced by a solution to said system of equations obtained in some preceding executed step of solving.

25. The method of claim 1 wherein said step of solving the system of equations may include using a set of formulas analytically representing the solution to said system of equations.

26. The method of claim 1 wherein said step of solving the populated system of equations is comprised of two operations and;
   further wherein the first operation returns an approximate values for components of the solution vector; and still further wherein the second operation returns accurate values for components of the solution vector.

27. The method of claim 26 further including using the approximate values of the vector of solution generated by the first procedure for inputting the second operation to return accurate components of the solution vector, thereby increasing computing speed of the method of the present invention.

28. The method of claim 26 further including using the approximate values of the vector of solution for generating the guess values vector inputting the numerical solver returning accurate components of the solution vector.

29. The method of claim 1, further comprising the step of recording the outputted values of the measured variables in a computer readable medium.

30. A method for measurement of positional coordinates, thickness and electromagnetic parameters of a flat conductive material, comprising the steps of:
generating an electromagnetic system of oscillating electromagnetic fields interacting with the sample portion of the material from a pair of sources positioned remotely on opposing sides of the sample portion;
measuring component values of impedance of the electromagnetic system made by each remote source of electromagnetic field and the material sample;
populating a system of equations including the measured impedance component values and a theory of electromagnetism-based mathematical model of the electromagnetic system;
solving the system of equations to calculate values of the sample portion distance to each source of EMF, thickness of the sample material in proximity to a point of projection on the sample material by each source of EMF, and the sample material's electromagnetic parameters;
outputting the calculated values;
repeating the steps of generating, measuring, populating, solving, outputting and repeating.

31. The method of claim 23, wherein the pair of sources are coaxially located on opposing sides of the sample portion.

32. A method for adjusting the thickness of flat, electrically conductive material under compressive and tensile forces, comprising the steps of:
generating an oscillating electromagnetic field (EMF) interacting with a sample portion of flat, electrically conductive material, from a source remotely positioned from the sample portion;
measuring component values of impedance of an electromagnetic system including the source of the EMF and the sample portion;
populating a system of equations including the measured component values and a theory of electromagnetism-based mathematical model of the electromagnetic system;
solving the system of equations to calculate values of a distance between the sample portion and the source and thickness of the sample portion in proximity to a point of projection of the source in to the sample portion;
using the calculated values for adjusting compressive and/or tension forces on the material;
repeating the steps of measuring, populating, solving, using and repeating.

33. A method for recording quality control measurements of thickness of a flat conductive material, comprising the steps of:
generating an oscillating electromagnetic field (EMF) interacting with a sample portion of flat conductive material, from a source remotely positioned from the sample portion;
measuring component values of impedance of an electromagnetic system including the source of the EMF and the sample portion;
populating a system of equations including the measured component values and a theory of electromagnetism-based mathematical model of the electromagnetic system;
solving the created system of equations to calculate values of a distance between the sample portion and the source and thickness of the sample portion in proximity to a point of penetration of the sample portion by a normal vector to the source;
recording the calculated values on a computer readable medium; and
repeating the steps of measuring, populating, solving, outputting and repeating.

34. The method of claim 26, wherein the material is metal and further wherein the compressive and tension forces are created in a rolling process.

35. A system for measuring positional coordinates and thickness of a flat conductive material, comprising:
an electromagnetic source adapted for generating an oscillating electromagnetic field (EMF) interacting with a sample portion of flat conductive material, wherein the source is remotely positioned from the sample portion;
circuitry adapted for measuring component values of impedance of an electromagnetic system including the source of the EMF and the sample portion; and
a computing system for solving a system of equations including a theory of electromagnetism-based mathematical model of the electromagnetic system and the measured component values to calculate values of a distance between the sample portion and the source, thickness of the sample portion in proximity to a point of projection of the source onto the material sample portion and electromagnetic properties of the sample portion.

36. The system of claim 35 wherein the computing system is adapted to receive initial estimates of a positional coordinate and a thickness of the sample portion for purposes of populating the system of equations including a theory of electromagnetism-based mathematical model of the electromagnetic system.

37. The system of claim 36 wherein the positional coordinate is a distance between the source and the point of projection on a surface of the sample portion.

38. The system of claim 35 wherein the computing system is adapted for receiving initial estimates of parameters and characteristics of said electromagnetic system.

39. The system of claim 38 wherein said parameters include electrical conductivity and magnetic permeability of the material sample and said characteristics are the components of the theoretical impedance of said electromagnetic system, and further wherein the components of said theoretical impedance are predetermined for said measuring system.

40. The system of claim 35 wherein the computing system includes a recursive numerical solver.

41. A system for measuring positional coordinates and thickness of a flat conductive material, comprising:
a pair of electromagnetic sources adapted for remote positioning on opposing sides of a sample portion of flat conductive material and for generating oscillating electromagnetic fields (EMF) interacting with the sample portion of flat conductive material;

circuitry adapted for measuring component values of impedance of an electromagnetic system made by each source of the pair of electromagnetic sources and the sample portion; and a computing system for solving a system of equations including a theory of electromagnetism-based mathematical model for each electromagnetic system and the measured component values to calculate values of a distance between the sample portion and each source, thickness of the sample portion in proximity to a point of projection of each source onto the material sample portion and electromagnetic properties of the sample portion.

42. A system for adjusting the thickness of flat, electrically conductive material under compressive and tensile forces, comprising:

an electromagnetic source adapted for generating an oscillating electromagnetic field (EMF) interacting with a remotely positioned sample portion of flat conductive material;

circuitry adapted for measuring component values of impedance of an electromagnetic system including the source of EMF and the sample portion; and a computing system for solving a system of equations including a theory of electromagnetism-based mathematical model of the electromagnetic system and the measured component values to calculate values of a distance between the sample portion and the source, thickness of the sample portion in proximity to a point of projection of the source onto the material sample portion and electromagnetic properties of the sample portion. means for using the calculated values for adjusting compressive and/or tension forces on the material.

43. The system of claim 42 wherein the computing system is adapted to receive initial estimates of a positional coordinate and a thickness of the sample portion for purposes of populating the system of equations including a theory of electromagnetism-based mathematical model of the electromagnetic system.

* * * * *

UNITED STATES PATENT AND TRADEMARK OFFICE
CERTIFICATE OF CORRECTION

PATENT NO. : 8,174,258 B2  
APPLICATION NO. : 12/426880  
DATED : May 8, 2012  
INVENTOR(S) : Alexander M. Raykhman It is certified that error appears in the above-identified patent and that said Letters Patent is hereby corrected as shown below:

In Column 18, line 11 (claim 42), "sample portion." should read -- sample portion; --

Signed and Sealed this  
Twenty-sixth Day of June, 2012

David J. Kappos  
*Director of the United States Patent and Trademark Office*